United States Patent
Michaelson et al.

(10) Patent No.: US 7,309,472 B2
(45) Date of Patent: Dec. 18, 2007

(54) STERILIZATION APPARATUS FOR ORTHODONTIC BANDS

(76) Inventors: Dennis J. Michaelson, 1570 Satterfield, Pocatello, ID (US) 83201; Jeffrey W. Mix, 2271 Overland Ave., Suite #4, Burley, ID (US) 83318

(*) Notice: Subject to any disclaimer, the term of this patent is extended or adjusted under 35 U.S.C. 154(b) by 673 days.

(21) Appl. No.: 10/050,400

(22) Filed: Jan. 15, 2002

(65) Prior Publication Data
US 2002/0064490 A1    May 30, 2002

Related U.S. Application Data

(63) Continuation of application No. 09/560,591, filed on Apr. 28, 2000, now Pat. No. 6,368,565.

(51) Int. Cl.
*A61L 2/00* (2006.01)
*A61B 19/02* (2006.01)
*A47F 7/00* (2006.01)
*E05D 7/10* (2006.01)
*A45F 5/00* (2006.01)

(52) U.S. Cl. ............ 422/297; 422/300; 422/102; 422/104; 220/528; 220/754; 206/63.5; 206/363; 206/368; 206/369; 206/370; 206/438; 206/366; 211/49.1; 211/50; 248/250; 16/265; 16/366; 224/270; 224/271

(58) Field of Classification Search ............ 422/297, 422/300, 102, 104, 20, 25–26, 28, 40; 220/528, 220/754; 206/63.5, 363, 368–370, 438, 366; 211/49.1, 50; 248/250; 16/365–366, 368; 224/270–271; 294/137; D7/622; 312/31, 312/35, 114, 117
See application file for complete search history.

(56) References Cited

U.S. PATENT DOCUMENTS

| | | | | |
|---|---|---|---|---|
| 2,680,522 A | * | 6/1954 | Temple ...................... 108/59 |
| 3,007,708 A | * | 11/1961 | Ochs ..................... 280/33.998 |
| 4,327,060 A | | 4/1982 | Nish ......................... 422/300 |
| 4,364,150 A | * | 12/1982 | Remington ................. 16/409 |
| 4,535,908 A | * | 8/1985 | Dabich ..................... 220/484 |
| 4,541,992 A | * | 9/1985 | Jerge et al. ................ 422/300 |
| 4,552,163 A | | 11/1985 | Biancalana et al. ........ 134/100 |
| 4,617,178 A | | 10/1986 | Nichols ..................... 422/310 |
| 4,658,467 A | * | 4/1987 | Stolarz ..................... 16/114.1 |
| 4,661,326 A | | 4/1987 | Schainholz ................ 422/310 |
| 4,671,943 A | | 6/1987 | Wahlquist ................. 422/300 |
| 4,723,693 A | * | 2/1988 | DeCoster ................... 222/483 |
| 4,752,444 A | | 6/1988 | Bowen et al. .............. 422/28 |
| 4,774,063 A | | 9/1988 | Runnells ................... 422/297 |
| 4,804,943 A | * | 2/1989 | Soleimani ................ 340/539.1 |
| 4,915,913 A | * | 4/1990 | Williams et al. ............ 422/119 |
| 4,971,774 A | | 11/1990 | Schwanke et al. ......... 422/310 |

(Continued)

*Primary Examiner*—William H. Beisner
*Assistant Examiner*—Monzer R. Chorbaji
(74) *Attorney, Agent, or Firm*—Frank J. Dykas; Stephen M. Nipper; Dykas, Shaver & Nipper, LLP

(57) ABSTRACT

A sterilization system for dental and orthodontic tools is provided with a transport rack dimensionally sized to hold a plurality interchangeable cassettes. The interchangeable cassettes are designed and intended to hold kits of dental or orthodontic tools and are provided with top opening, double-hinged covers which lay flat on the surface when opened and used at a dental workstation.

14 Claims, 11 Drawing Sheets

U.S. PATENT DOCUMENTS

| | | | |
|---|---|---|---|
| 5,006,066 A * | 4/1991 | Rouse | 433/77 |
| 5,039,495 A | 8/1991 | Kutner et al. | 422/299 |
| 5,154,611 A * | 10/1992 | Calvin | 433/77 |
| 5,176,884 A | 1/1993 | Taschner et al. | 422/292 |
| 5,184,046 A | 2/1993 | Campbell | 315/111.21 |
| 5,215,726 A * | 6/1993 | Kudla et al. | 422/297 |
| 5,372,787 A | 12/1994 | Ritter | 422/119 |
| 5,407,354 A | 4/1995 | Fife | 433/116 |
| 5,480,302 A | 1/1996 | Fife | 433/116 |
| 5,482,067 A * | 1/1996 | Wittrock et al. | 137/135 |
| 5,543,119 A | 8/1996 | Sutter et al. | 422/299 |
| 5,641,065 A | 6/1997 | Owens et al. | 206/370 |
| 5,743,734 A | 4/1998 | Heath et al. | 433/77 |
| 5,759,502 A * | 6/1998 | Spencer et al. | 422/300 |
| 5,771,537 A * | 6/1998 | Ho | 16/410 |
| 5,858,303 A | 1/1999 | Schiffmann et al. | 422/21 |
| 5,871,702 A | 2/1999 | Kutner et al. | 422/299 |
| 5,918,740 A | 7/1999 | Berry, Jr. | 206/369 |
| 5,961,937 A | 10/1999 | Gobbato | 422/300 |
| 6,010,670 A | 1/2000 | Berry, Jr. | 212/325 |
| 6,368,565 B1 * | 4/2002 | Michaelson et al. | 422/300 |

* cited by examiner

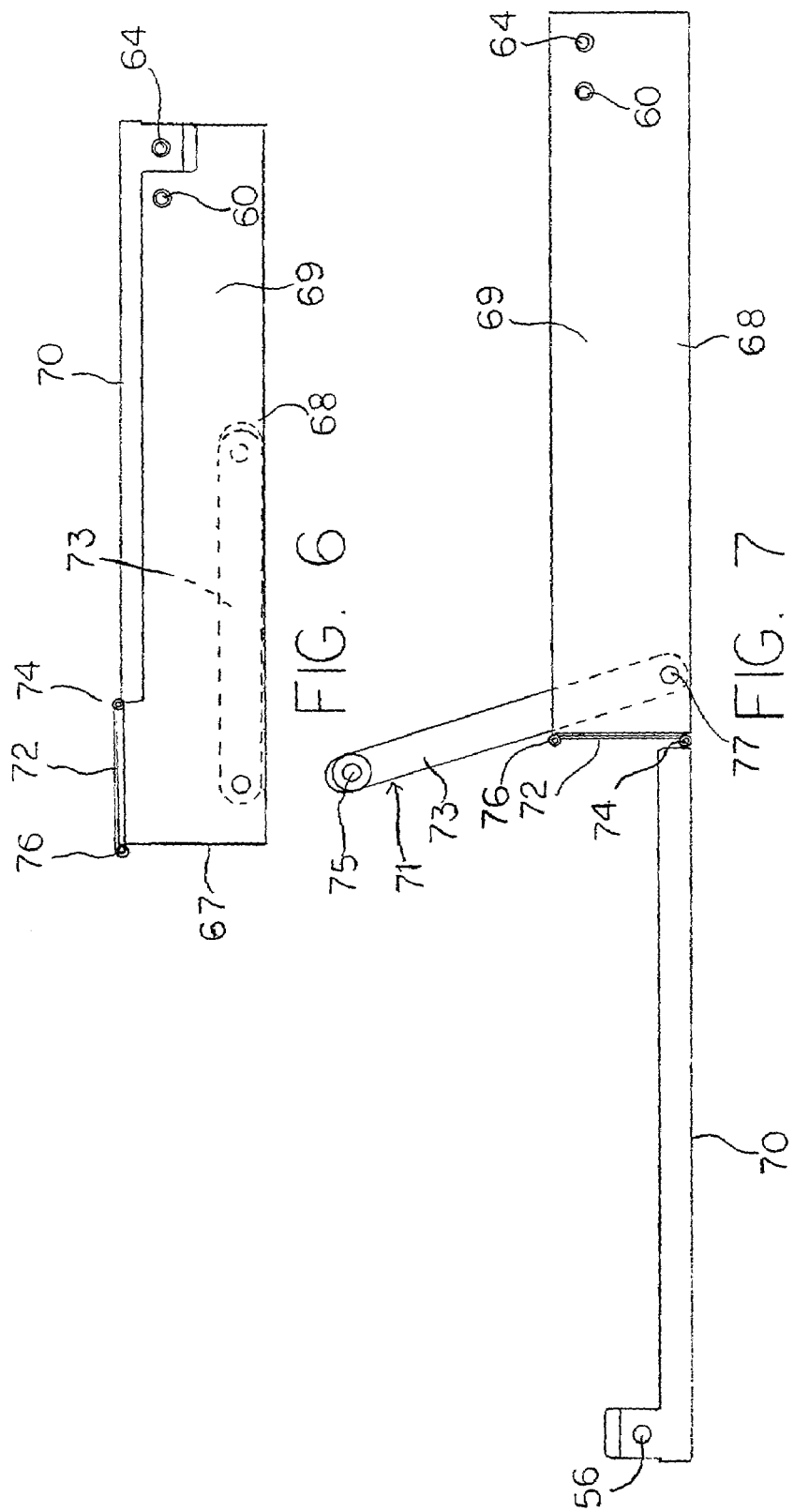

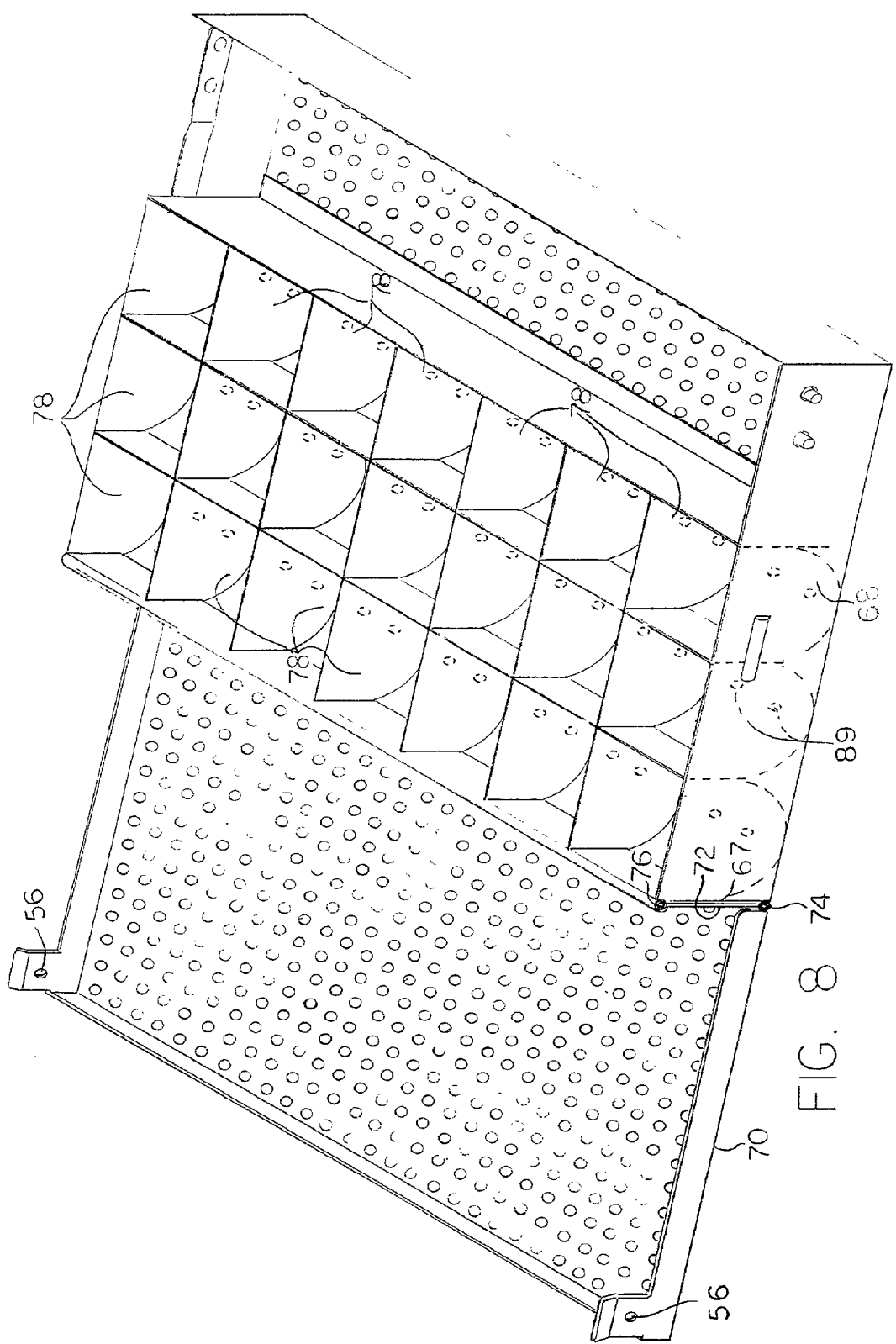

US 7,309,472 B2

STERILIZATION APPARATUS FOR ORTHODONTIC BANDS

PRIORITY

This application is a continuation application filed under the provisions of 37 CFR 1.53(b) from a non-provisional utility patent application filed Apr. 28, 2000 Ser. No. 09/560,591 now U.S. Pat. No. 6,368,565 entitled STERILIZATION APPARATUS FOR DENTAL AND ORTHODONTIC TOOLS incorporated herein by reference.

BACKGROUND OF THE INVENTION

1. Field of the Invention

The present invention generally relates to a cassette and tray system wherein cassettes of varying sizes are used to hold collections of orthodontic or dental tools for use in the sterilization process.

2. Background Information

While the human mouth is hardly a sterile environment, there is a need to protect patients from the transmission of infectious diseases from one patient to another through the use of contaminated orthodontic or dental tools. Gone are the days when the orthodontist or dentist merely washed his hand tools between use on patients. Such organizations as the American Dental Association, American Association of Orthodontics, the Federal Occupational Safety and Health Administration and the Center for Disease Control are all actively working to set standards and guidelines to insure the safety of the patients as well as the orthodontists, dentists, and their assistants.

At the present time, there are three standardized methods of sterilizing dental and orthodontic hand tools. In each of the three, the hand tools are first dropped into a tank containing water and perhaps solvents, and ultrasound is applied to agitate the fluid to wash and remove the debris remaining on the hand tools from their last use. The tools are left somewhat damp then dried and heated in some manner to a temperature sufficient to destroy any microorganisms or viruses on the hand tools. The three primary methods of doing this are the use of dry heat, heat wherein the hand tools are heated to a temperature of at least 365° Fahrenheit for six minutes, or the use of steam under pressure in an autoclave system. The time to sterilize, using a steam autoclave system, depends on heat and pressure and whether the instruments are wrapped or not. A common wrapped cycle is 270° at 27 p.s.i. for fifteen minutes. An unwrapped cycle at the same temperature and pressure would be for three minutes. In some sterilization processes, chemicals are applied to the hand tools as an intermediate step between the ultrasonic bath and the heating. A third method of sterilization is a chemical clave wherein a heated, controlled atmosphere of various gases is used to heat the hand tools held within sealed sterile paper bags.

The problem is that orthodontists and dentists with busy professional practices will see many patients in any given work day, indeed it is not unusual for an orthodontist to see in excess of 100 patients per day. A lot of hand tools are used each day, and they are generally collected throughout the day and recycled, in bulk, through the sterilization process. In a busy orthodontics practice, it is not unusual to have one assistant dedicated solely to collecting hand tools and sterilizing them on a full time basis.

In the typical prior art orthodontic or dental practice, once the tools have been resterilized, they are simply returned to the workstation and placed where they are readily available for reuse. However, this is a source of contamination. If, for example, a dentist is working on a patient's teeth and calls to his assistant for a new and different tool, and the assistant reaches into the drawer to retrieve the tool wearing a latex glove that has been contaminated with the body fluids of the patient, the assistant can transfer those contaminants to other, unused tools which were previously sterilized. Inevitably, conditions arise where contaminated hands are used to retrieve tools from the drawers.

Accordingly, what is needed is a cassette system wherein cassettes can be preloaded with standard sets of tools for use in either orthodontic or dental practices, and kept together as a set throughout the sterilization process. What is also needed is a means of collecting the cassettes into convenient packages where they can be batch fed through the ultrasonic bath and heat applications, and remain in a sterile condition when they are returned as a set to the workstation. Additionally, this cassette collection system must require a minimum amount of counter space at the vicinity of the dental chair, either on the bracket table or the work side unit, and finally, the cassettes must be configured such that they remain stable and flat on the countertop surface when opened so that they do not fall off the table onto the floor, or worse yet, the patient.

Additional objects, advantages and novel features of the invention will be set forth in part in the description as follows, and in part will become apparent to those skilled in the art upon examination of the following, or may be learned by practice of the invention. The objects and advantages of the invention may be realized and attained by means of the instrumentalities and combinations particularly pointed out in the appended claims.

SUMMARY OF THE INVENTION

These objects are achieved through use of a transport rack and a plurality of cassette systems. The transport rack is formed of sidewalls, a back wall, and a bottom wall which are all interconnected to form a rigid transport rack. The tray is provided with a plurality of shelves for holding cassettes which are inserted through the front of the transport rack. The walls and shelves of the transport rack are provided with a plurality of holes or slots through which fluids and debris cleaned during the ultrasonic cleaning portion of the sterilization process may readily pass.

The transport rack is also provided with two flanges which are attached to the top of the sidewalls. The transport rack is dimensionally sized to a preselected dimension as to provide for interchangeability of cassettes as is later described.

There are two basic designs for the cassettes. In the first design, first and second hinges are provided, with the first interconnecting the side wall of the cassette to a hinge plate, and the second hinge interconnecting the hinge plate to the top cover in such a manner that when the top cover is opened, it may be levered open from the top edge of the back wall and the hinge plates swinging down such that the cover lies flat against the surface upon which the cassette is resting. Like the transport rack, slots or holes are provided to allow for the passage of fluid and debris out from the cassette.

In the second design for the cassettes, the top cover is divided into two portions, the first being the cover portion and the second being the hinge plate with the hinge plate attached to the top of the side wall and the second hinge interconnecting the hinge plate to the remainder of the cover. As in the first design, the double hinge arrangement allows for the cover to be opened and laid flat against the surface upon which the cassette is resting.

In a third design, a fold down pliers rack is provided, which can be tilted up and used to hold pliers in a generally vertical orientation wherein the do not become entangled with each other.

In all designs, two opposing latch assemblies are provided so that equal and opposite pressure must be applied to the latches in order to unlatch the top cover so as to open it. The purpose of providing the double latches and the requirement for equal and opposite pressure is to prevent inadvertently pushing the transport rack off of the surface upon which it is resting since the use of both hands is required to open the latches.

The cassettes are sized in plurality of different sizes with the largest size and all intermediate sizes being full integer multiples of the smallest cassette size such that if the cassettes are used in a random manner, they can still be conveniently stacked to fully pack a transport rack prior to the sterilization process.

The cassettes are also provided with color-coded buttons fixed to the end walls so that the kits of dental tools that are contained within each cassette can be readily identified.

Two types of handles are provided, the first being a top handle which is provided with a pair of opposing plates which interfit underneath the flanges attached to the tops of the side walls along with a locking or insertion button to prevent the tray from sliding off of the handle plates. A side, levered handle is also provided with two insertion plates which also insert underneath and interfit underneath the flanges to permit withdrawal of the cassette from a sterilization device, which may be hot, having only a sidewall opening.

Still other objects and advantages of the present invention will become readily apparent to those skilled in this art from the following detailed description wherein I have shown and described only the preferred embodiment of the invention, simply by way of illustration of the best mode contemplated by carrying out my invention. As will be realized, the invention is capable of modification in various obvious respects all without departing from the invention. Accordingly, the drawings and description of the preferred embodiment are to be regarded as illustrative in nature, and not as restrictive.

BRIEF DESCRIPTION OF THE DRAWINGS

FIG. 6 is a side view of the second cassette in a closed configuration.

FIG. 7 is a side view of the second cassette in an open configuration.

FIG. 8 is a perspective representational view of the second cassette in an open configuration.

DESCRIPTION OF THE PREFERRED EMBODIMENTS

Figure 1:
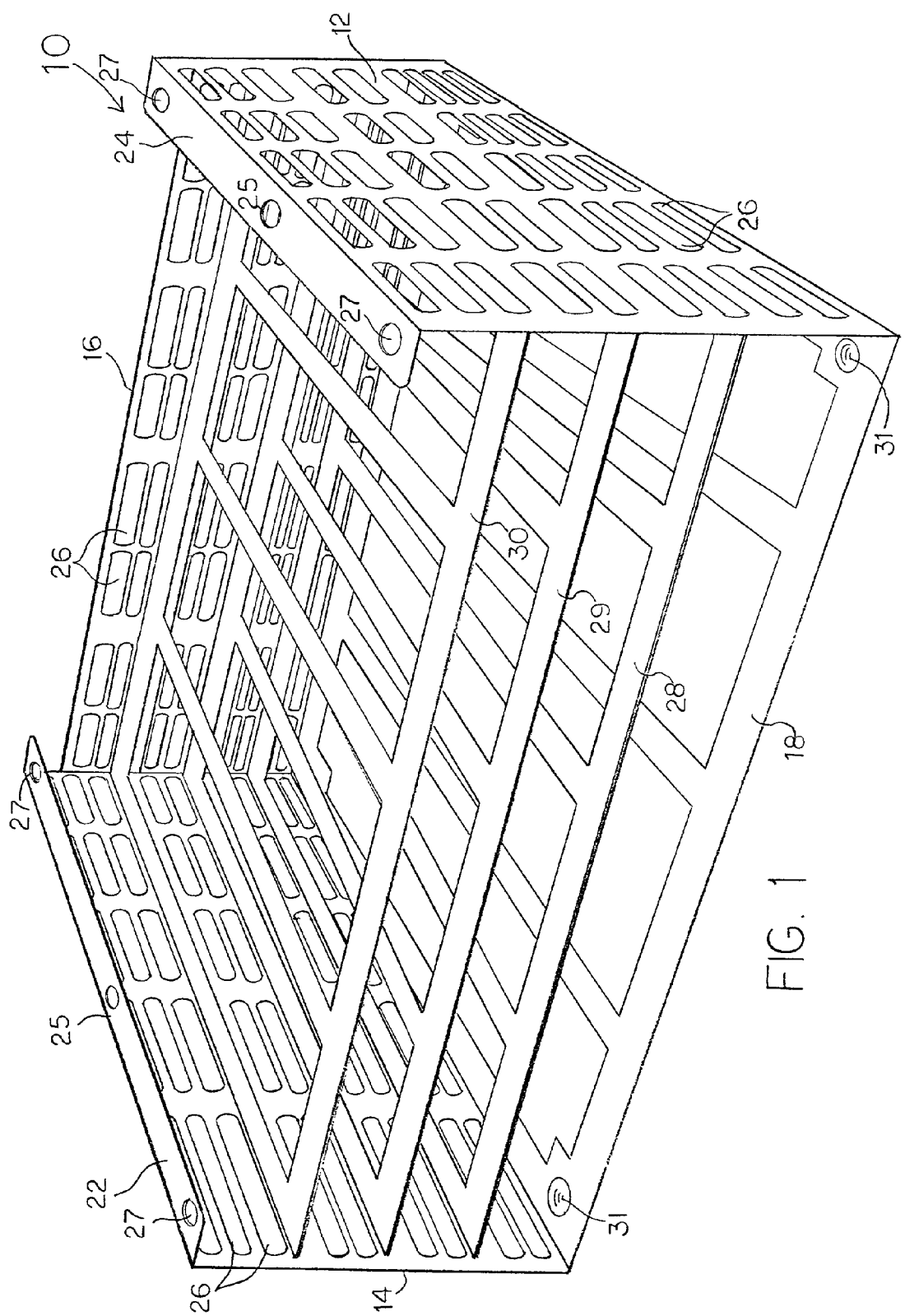
FIG. 1 is a perspective representational view of a transport rack.

While the invention is susceptible of various modifications and alternative constructions, certain illustrated embodiments thereof have been shown in the drawings and will be described below in detail. It should be understood, however, that there is no intention to limit the invention to the specific form disclosed, but, on the contrary, the invention is to cover all modifications, alternative constructions, and equivalents falling within the spirit and scope of the invention as defined in the claims.

First referring to FIG. 1, there is shown a transport rack 10, which is formed of side walls 12 and 14, back wall 16, and bottom wall 18, which are all interconnected to form a rigid transport rack. In FIG. 1, three shelves, first shelf 28, second shelf 29, and third shelf 30 are provided, and as a result four tiers of cassettes can be contained within transport rack 10. There is nothing particularly critical about the number of shelves, as this is merely the preferred embodiment. Depending upon the cassette tray configurations, transport rack 10 could be configured with any number of shelves, including none at all. It is also to be noted that all of the walls of transport rack 10 contain a plurality of holes or slots 26 through which fluids and debris cleaned during the ultrasonic cleaning portion of the sterilization process may readily pass.

Transport rack 10 is provided with two flanges, 22 and 24, which are attached to the top of sidewalls 14 and 12 respectively. Side handle insertion holes 27 in flanges 22 and 24 are provided at the front and back for receiving insertion pins 99 on side handle 90 as is later described and shown in FIG. 11. Additionally, side handle insertion holes are positioned to receive dimpled feet 31 when a plurality of transport racks 10 are stacked one atop the other. Top handle insertion holes 25 are provided at the general location of the center of gravity locations in flanges 22 and 24 for receiving insertion pins 88 of top handle 80 as is later described and shown in FIGS. 9 and 12. Transport rack 10 is fabricated to known and preselected dimensions as to provide for interchangeability of cassettes as is later described.

Figure 2:
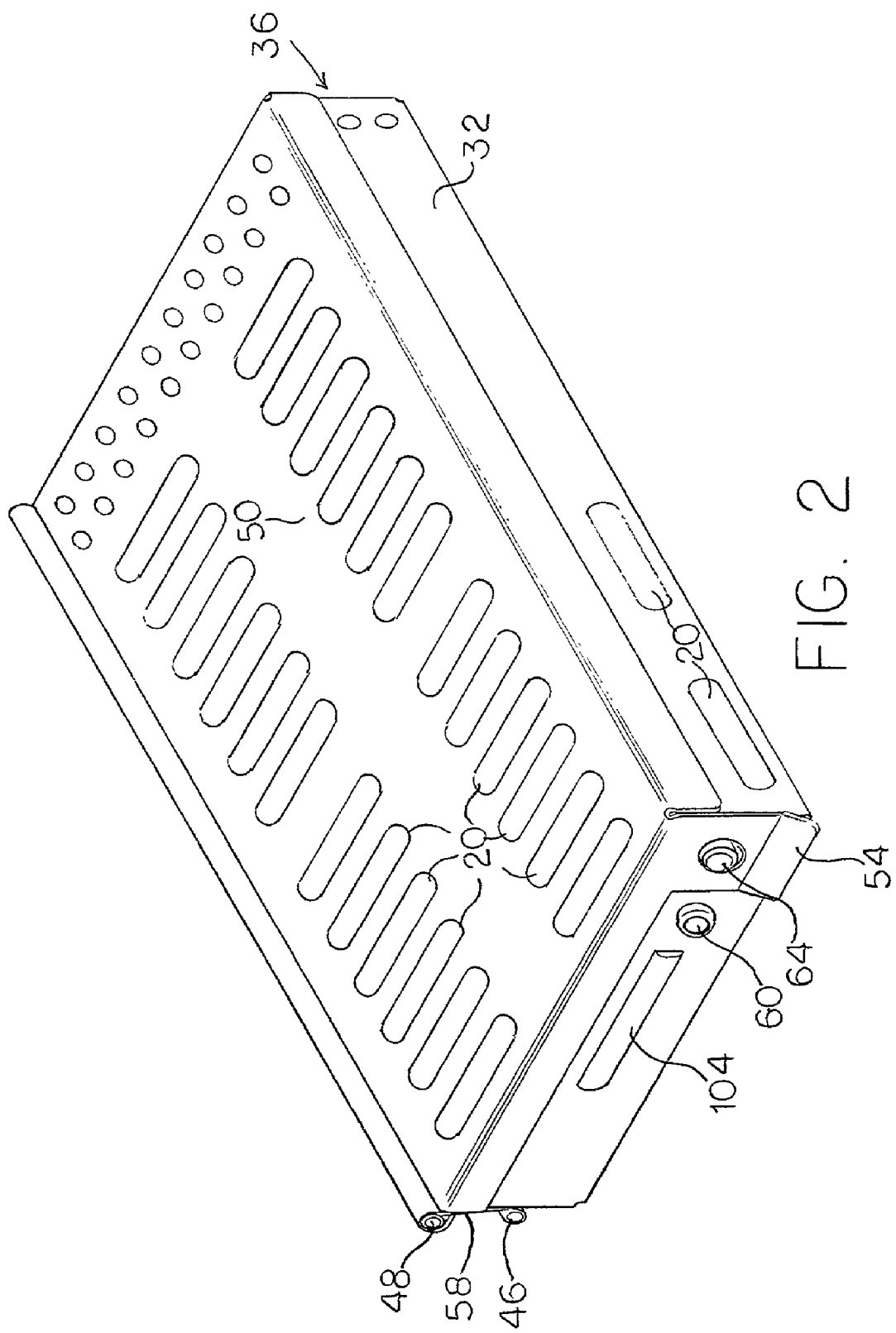
FIG. 2 is a perspective representational view of a first cassette in a closed configuration.
Figure 3:
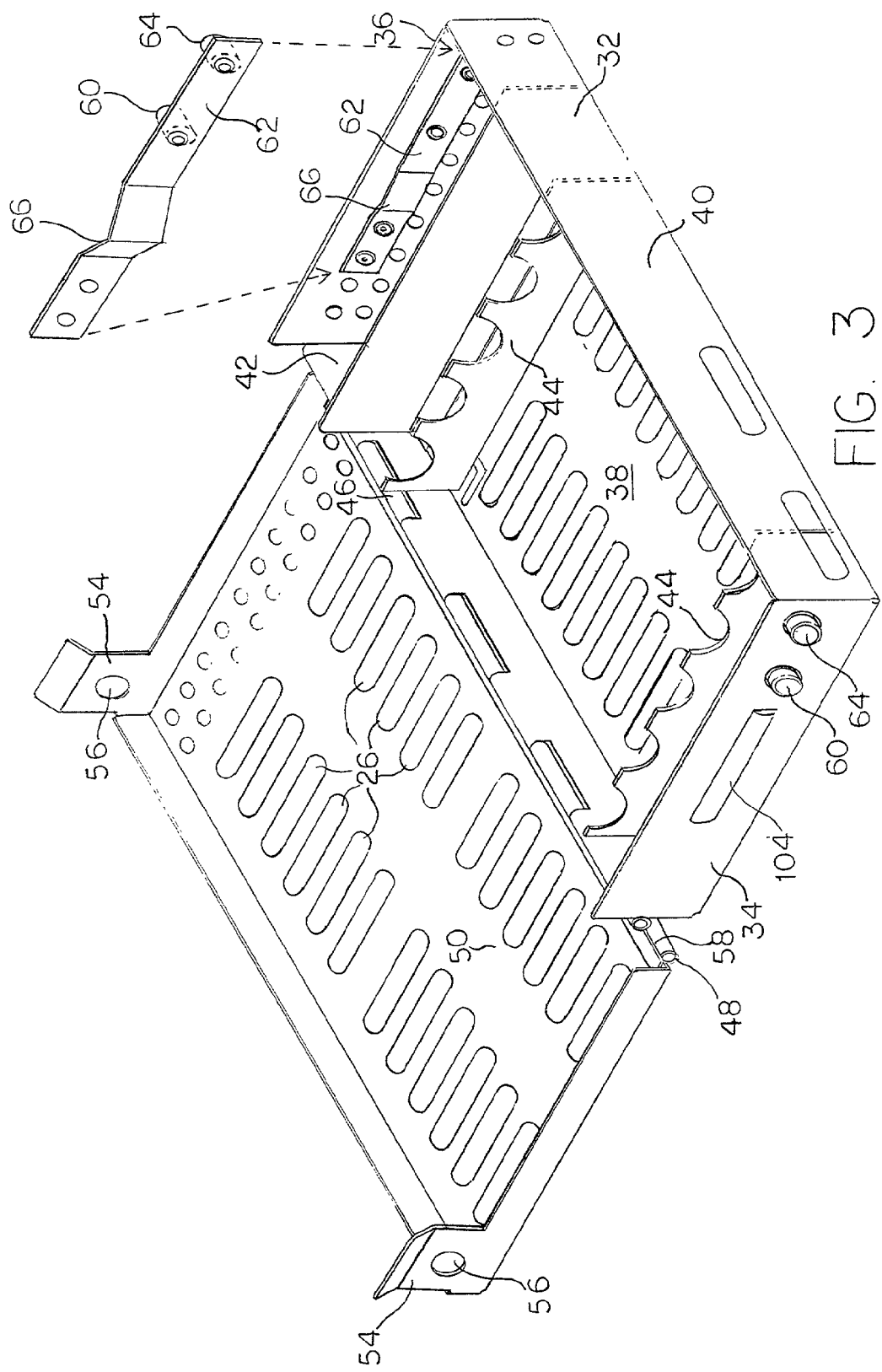
FIG. 3 is a perspective representational view of the first cassette in an open configuration.
Figure 4:
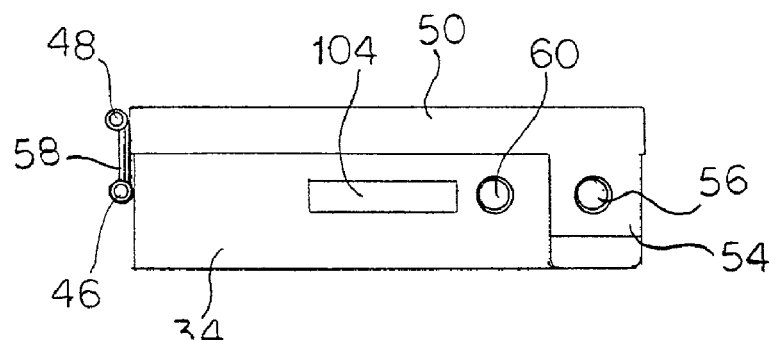
FIG. 4 is an end view of the first cassette in a closed configuration.

Shown in FIGS. 2 through 5 is a first cassette 32. It, like transport rack 10, is formed of stainless steel in the preferred embodiment, although other materials may be used to fabricate all of the parts of this sterilization system. In FIGS. 2 and 4, first cassette 32 is shown in its closed configuration, and in FIGS. 3 and 5, in its open configuration. First cassette 32 is formed of side walls 34 and 36 attached to bottom 38, front wall 40, and back wall 42. In this embodiment, tool brackets 44 are provided to hold the dental or orthodontic hand tools above the bottom 38.

Figure 5:
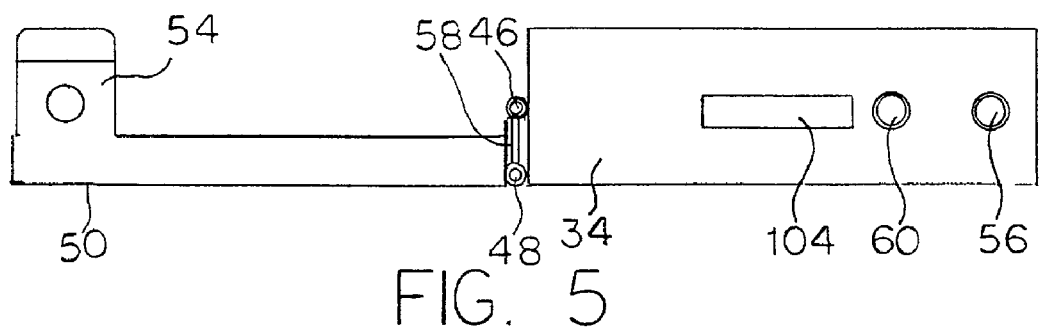
FIG. 5 is an end view of the first cassette in an open configuration.

First and second hinges 46 and 48 are also used to form a double hinge system for top cover 50. The purpose of the double hinge system is to ensure that the top cover 50 lies flat against the counter surface when cassette 32 is in the open configuration. In practice, it has been found that it is much more stable when it is laid flat as opposed to being levered open from the top edge of the back wall 42. First hinge 46 is attached at an intermediate, height position, halfway up the back of the back wall 46, and also to hinge extension plate 58 such that hinge extension plate will swing down as shown in FIG. 5 to enable top cover 50 to rest flat and securely against the countertop. As with the transport rack, slots or holes 20 are provided to allow for the passage of fluid and debris out from first cassette 32. Also, as can be seen most clearly in FIG. 3, a pair of opposing latch assemblies are provided for holding the top cover firmly latched to first cassette 32. It is formed of a leaf spring 62 which is spot-welded to an end wall. Leaf spring 62 has attached to it a release button 60, and a latch detent 64.

Top cover 50 is provided with lid extensions 54, having receiving holes 56 for receiving latch detent 64 and to secure top cover 50, first cassette 32.

The purpose of two opposing latch assemblies is so that equal opposing pressure is applied to first cassette 32 when both release buttons 60 are pushed in to withdraw latch detent 64 from receiving holes 56, in equal inward motion. Thus the first cassette 32 will remain stable and stationary when it is being opened at the dental or orthodontic workstation. Again, this increases the stability and decreases the likelihood that the cassette will move, either falling itself to the floor or worse yet, pushing something else off of the workstation/countertop onto the floor.

Also in the preferred embodiment, color-coded bars 104 are fixed to the end walls of first cassette 32. These can be made of thermal plastic or other heat resistant materials, or even simply painted metal. Color-coding can be a convenient way of quickly identifying certain specialized sets of hand tools that are used for specific procedures. Obviously, other coding indicia may be used.

In FIGS. 6, 7, and 8, there is shown second cassette 68. There are a number of different features shown in second cassette 68 that are not shown in first cassette 32. The first is that the double hinge assembly for the top cover divides the top cover into two portions, top portion 70 and drop plate 72. Dimensionally, drop plate 72 is the same size as back wall 67 of second cassette 68. Thus, when the top cover 70 is opened as shown in FIG. 7, two things occur. First its footprint on the countertop is reduced, and secondly, it lays flat against the counter top.

Hinge assemblies 74 and 76 are identical to those shown and described for first cassette 32 are provided for second cassette 68.

In an alternative embodiment for second cassette 68, drop plate 72 can be made longer so that hinge 74 extends below the bottom of second cassette 68, thus enabling the user to fold top cover 70 underneath second cassette 68. In this configuration, lid extensions 54 will serve to tip second cassette 68 to an angle wherein the contents can be more easily viewed. In a third configuration, additional lid extensions 54 can be added to top cover 70 to serve as support legs so as to enable the user to flip top cover 70 completely under second cassette 68 and still rest flat on its support legs.

Figure 7A:
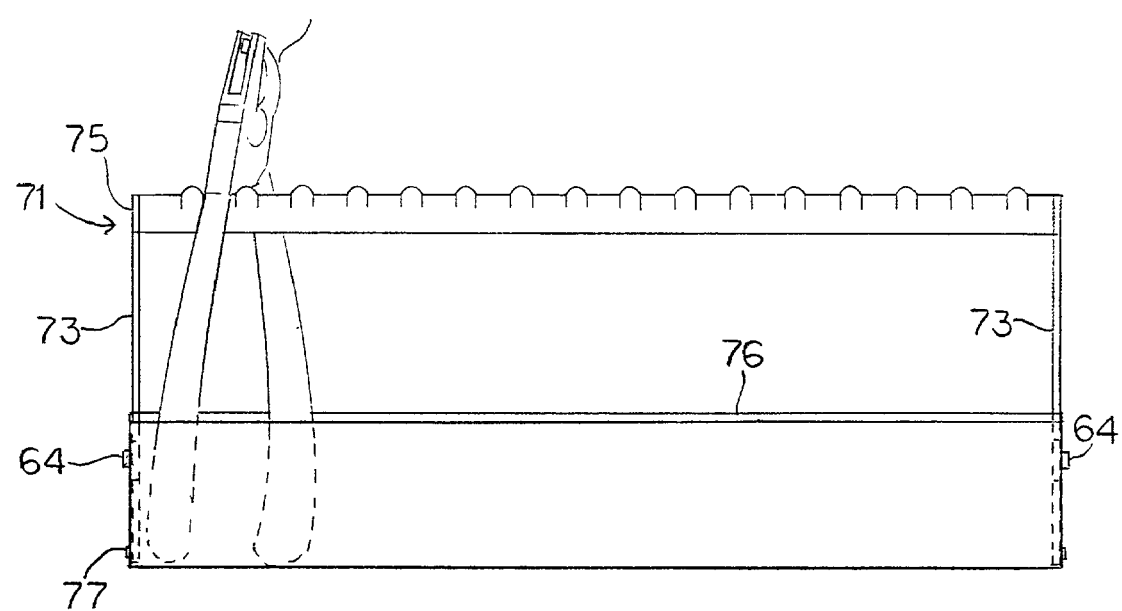
FIG. 7A is a front view of the second cassette in an open configuration with a pliers rack tilted up.

Also, as shown in FIGS. 6, 7 and 7A, a flip up pliers rack 71 formed of two pivotable arms 73, each hinged by pins 77 to opposing side walls 69 and cross brace 75 may be provided for second cassette 68. During the sterilization process it lays flat inside second cassette, and is flipped up for use where it rests by gravity against back wall 67. Other ways of flipping and holding pliers rack 71 in an up position include clips and latches This enables the user to hang pliers in an upright position during treatment of the patient. It allows for much easier identification of each pliers during the treatment process. After each use the pliers is hung on the pliers rack. If there is no pliers rack, the pliers, after each use, are placed back in the bottom of the cassette which in a short time becomes a jumbled pile of pliers. This makes identification of pliers more difficult as one requires different pliers for each part of any particular procedure. This wastes time hunting for pliers and can even pose a hazard to the user and the patient. One is more likely to get a puncture wound digging through a pile of sharp instruments than selecting pliers which are hung neatly from a pliers rack. Additionally if the pliers the user needs is on the bottom of the pile, the user will often, in an effort to put it out, inadvertently pull other pliers with which it has become entangled. If the cassette is on a tray or shelf over the patient's face, a second pliers could be inadvertently pulled out of the pile and onto the patient's face. After the procedure in which the pliers are used is over, the pliers are laid back down in the cassette, the pliers rack is pivoted to its storage position, the cover closed, and the cassette returned to the transport rack 10.

In another embodiment, as shown in FIG. 8, a plurality of divider plates 78 may also be provided within second cassette 68. In this configuration, second cassette 68 is called a band, or crown, box. These divider plates 78 provide an array of pockets into which metal orthodontic tooth bands, or metal temporary dental crowns, can be stored in a sorted-by-size fashion and even sterilized along with second cassette 68. Drain holes 89 are provided at the bottom of each pocket. The bottom of each pocket may also be provided with a rounded surface to make retrieval of individual bands or crowns easier.

Currently practitioners use a band or crown box that is not heat sterilizable. In use, various sizes of orthodontic bands or temporary crowns are tried on the tooth being treated. The bands or crowns are taken out of the box with sterile tweezers so as to not contaminate the others that are still in the box. Tweezers are also used in the mouth during these procedures. Often the two tweezers are confused which inevitably causes contamination of the remaining bands or crowns. If this happens the sizes not used must be removed from the non-sterilizable band or crown box, sterilized in bulk, resorted by size and returned to the band or crown box. Also, with the prior art band or crown box, bands or crowns that were placed in the mouth, but not selected for use, must be kept separate from the remaining bands or crowns still in the band or crown box. There must also be later sterilized in bulk, resorted and returned to the band or crown box. This is labor intensive and therefor expensive.

By use of my divider plates 78, a sterilizable band or crown box is created. The amount of labor required to maintain sterilized bands or crowns is greatly reduced in that each time a band or crown of an inappropriate size is chosen, and contaminated in the mouth, it can be returned to its correct pocket, thus eliminating the time consuming resorting of bands or crowns sterilized in bulk. This immediate return of bands or crowns to the box is of no concern since the whole selection of bands or crowns in the box can be sterilized after each use. Obviously this also eliminates the concern of using non-sterile tweezers since all will be sterilized after each use.

Figure 9:
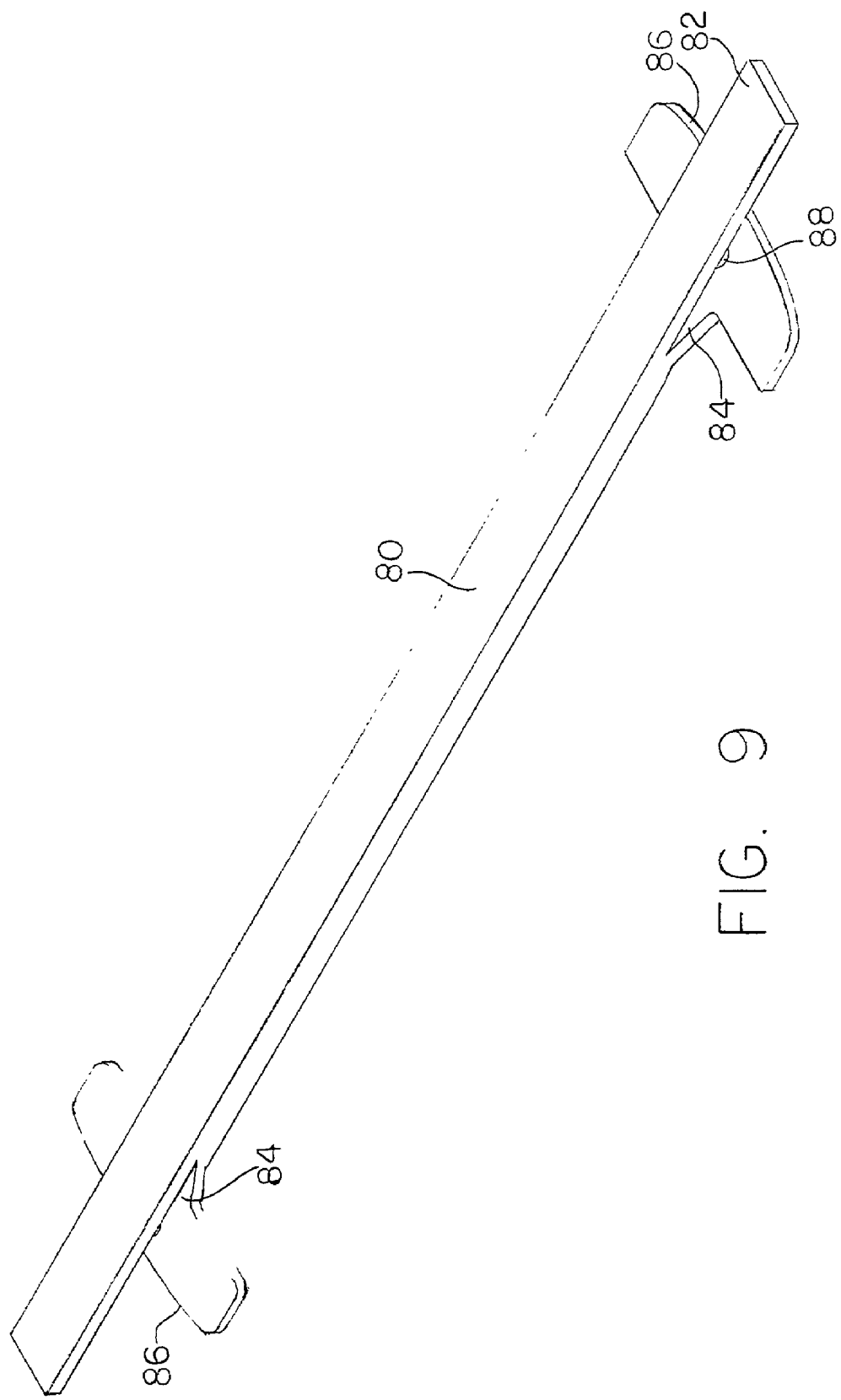
FIG. 9. is a perspective representational view of a top handle.
Figure 10:
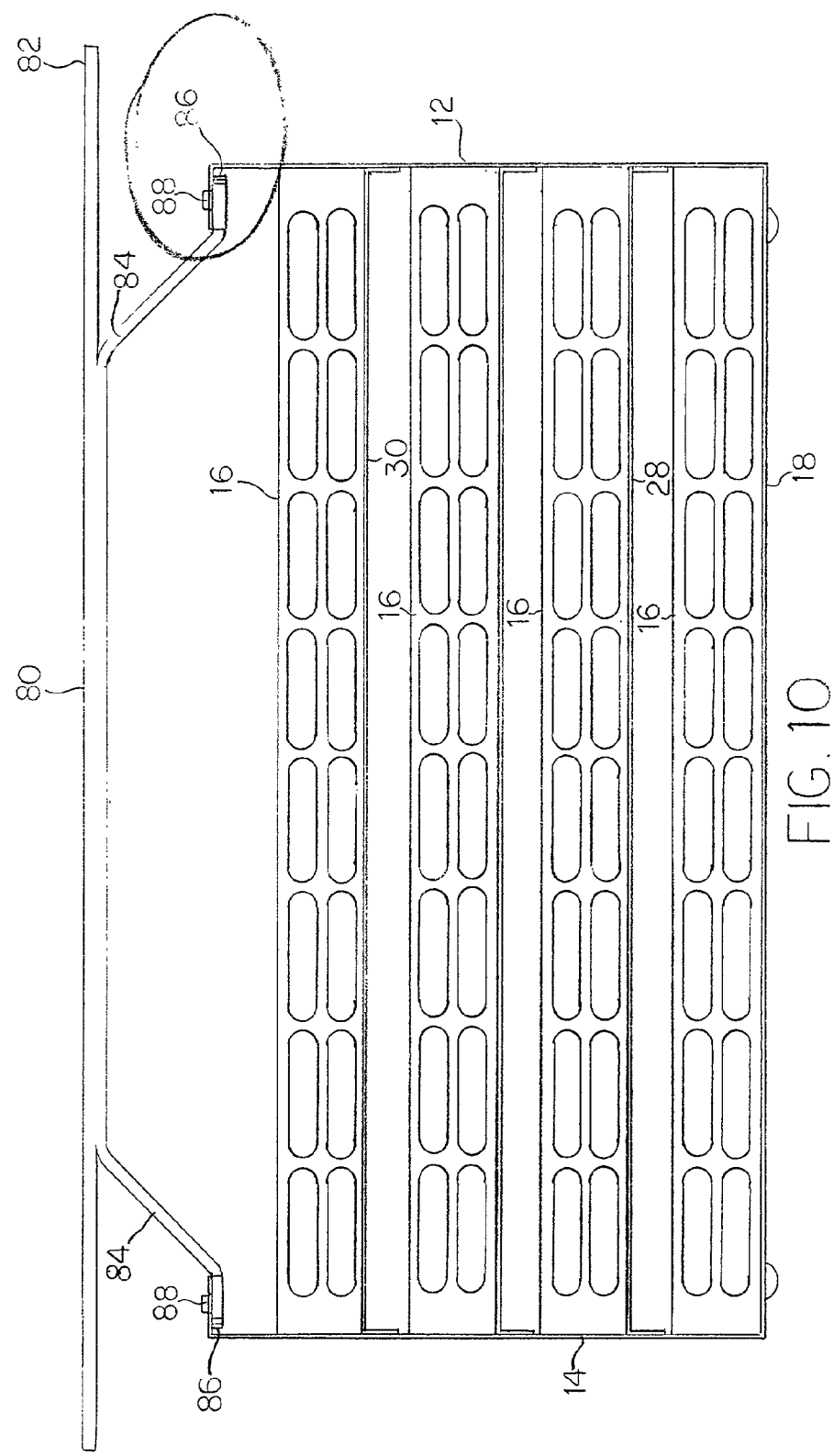
FIG. 10 is a front view of a transport rack and top handle.

As shown in FIGS. 9 and 10, there is provided a removable top handle for transport rack 10. The removable top handle is formed of top rail 82, which in the preferred embodiment is also configured in size and shape to be long enough so the ends provide a convenient holding bracket within an ultrasonic cleaner. This suspension is important because objects which rest on the bottom of an ultrasonic cleaner may reduce the vibration of the fluid which reduces cleaning effectiveness. Attached to and extending down from top rail 82 are opposing arms 84. Attached to arms 84 are plates 86, from which extend upwardly, engagement pins 88. Plates 86 are provided with curved outer edges which allows easier placement while engaging the top handle within flanges 22 and 24 of transport rack 10. If the outer edges of plates 86 are straight, the angle of insertion of top handle 80 cannot vary by much without binding on the side walls of transport rack 10. The top handle 80 is configured such that plates 86 will interfit underneath flanges 22 and 24 of transport rack 10 in a configuration where engagement pins 88 will extend up through holes 25.

Thus, the handle can be removed, if desired, when the cassette is in use at the workstation either as a source of sterilized tools and/or a receptacle for contaminated tools.

Figure 11:
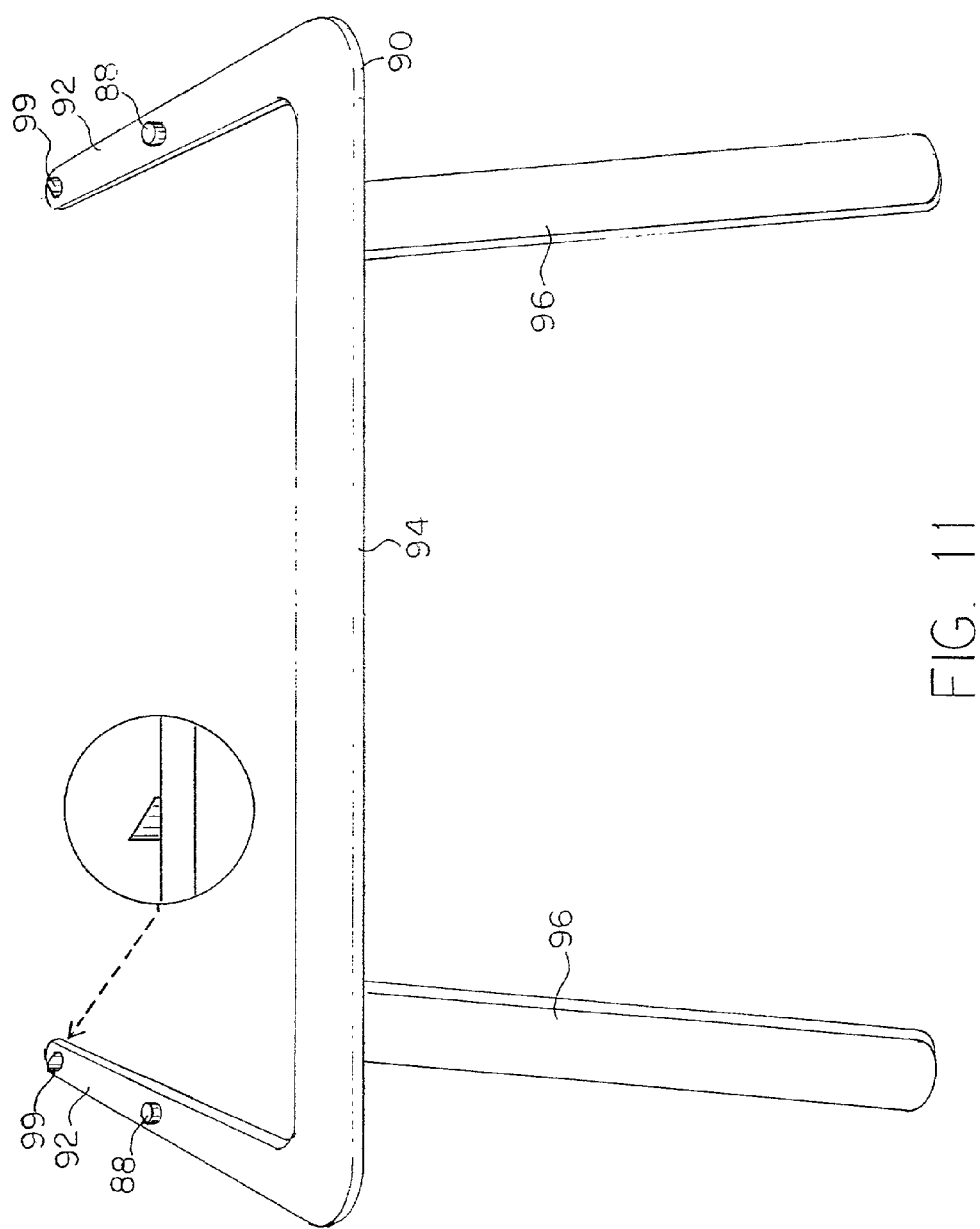
FIG. 11 is a perspective representational view of a side handle.

Most sterilization systems include a front opening door as opposed to a top opening door on the heat application apparatus. In such cases, a top handle is of little use, and for that reason a side handle is provided as shown in FIG. 11. Side handle 90 is formed of insertion rails 92 attached to front rail 94 to which is also attached lever handles 96. Insertion rails 92 are sized in the preferred embodiment to contact the transport rack back wall 16 before the operator grasping the lever handles 96 hands make contact with the hot transport rack 10. Like the top rail 80, side handle 90 is provided with insertion pins 88 which interfit within insertion holes 25 to prevent the insertion of side handle 90 far enough into transport rack 10 to a point where the user's fingers might contact a very transport rack 10 when removing it from the heat application apparatus. It also is provided with a pair of sloped insertion pins 99, each located at an end of the insertion rails 92. These are configured to interfit within holes 27 located at either the front or back ends of flanges 22 and 24. Holes 27 are located are located in these positions so as to enable the user to pick up the transport rack from either the front or the back. Picking up transport rack 10 from the back enables to user to tip transport rack 10 towards the user without the cassettes sliding out. Since transport rack 10, when fully loaded, may be heavy, the ability to tip transport rack toward the user is important, since if it tipped away from the user, the cassettes may slide out.

Figure 12:
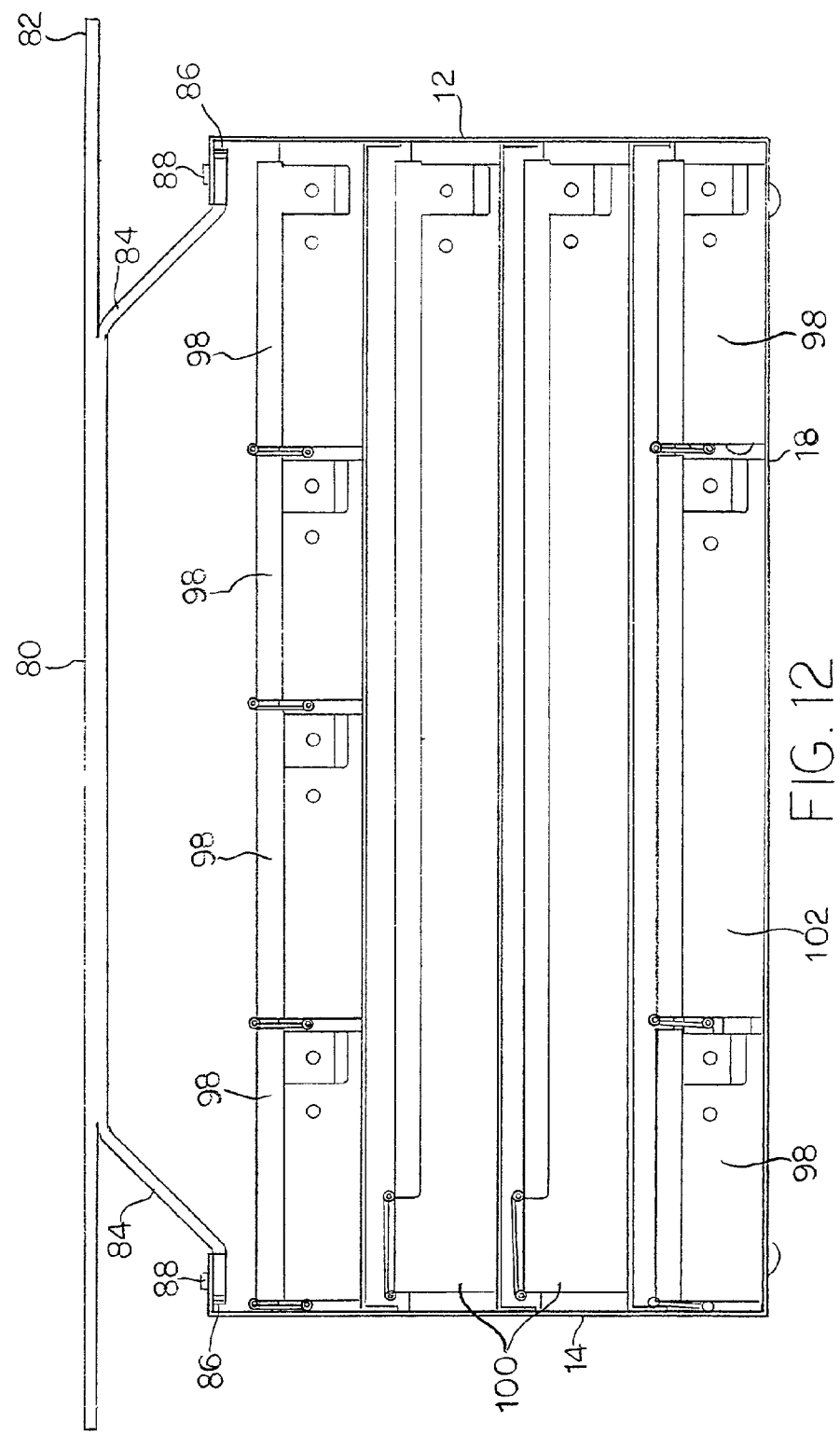
FIG. 12 is a front view of a transport rack holding a plurality of cassettes.

In FIG. 12 there is shown a front view of a loaded transport rack 10 in which the fully loaded transport rack 10 contains cassettes of various sizes. In this preferred embodiment, the preselected dimension for the width of transport rack 10 divides into convenient quarter sizes so that three different size cassettes can be utilized, without wasting space in transport rack 10. As is shown in FIG. 12, there is the first or smallest size cassette 98, an intermediate size cassette 102, and a full size cassette 100. Each of the cassettes is a full integer multiple of the smallest cassette with the largest cassette having the largest integer multiple. For example, the smallest cassette 98 can be sized to take up one quarter of the width of shelf, the intermediate cassette 102 one half, and the largest cassette 100 sized to completely fill the shelf by itself. This design has been found in practice to significantly minimize the amount of empty space in transport racks 10 during the sterilization process, which both speeds up the process and reduces the number of tools required to be kept in inventory.

While there is shown and described the present preferred embodiment of the invention, it is to be distinctly understood that this invention is not limited thereto but may be variously embodied to practice within the scope of the following claims.

From the foregoing description, it will be apparent that various changes may be made without departing from the spirit and scope of the invention as defined by the following claims.

We claim:

1. An apparatus for sterilizing dental or orthodontic tools, which comprises:
    a rigid non-folding transport rack having a pair of opposing side walls, a bottom and a back wall, all interconnected and forming a generally rectangular box of a pre-selected dimension which is open to the front and the top;
    each of said opposing side walls having a top edge;
    said opposing side walls, back walls and bottom each having a plurality of holes through which fluid and debris may pass;
    a pair of horizontally disposed, horizontally extending, basically flat side flanges, each of said side flanges being attached at said top edge of one of said opposing side walls, each of said opposing flanges having at least one hole therein, each of said holes defining a basically-planar open area where said basically-planar open area is basically parallel to said bottom, each of said side flanges being basically parallel to said bottom, said side flanges being basically perpendicular to said opposing side walls and basically perpendicular to said back wall;
    at least one shelf which is horizontally disposed and permanently attached to at least the opposing side walls and said back wall; and
    a plurality of cassettes adapted for placement upon said shelf and said bottom, each of said cassettes having a hinged top, and configured in size and shape to receive and hold dental or orthodontic tools.

2. The apparatus of claim 1 which further comprises a top handle having a horizontally oriented rail adapted to receive and vertically hold a plurality of dental or orthodontic pliers, said top handle having a pair of opposing and downwardly extending plates having upwardly extending pins configured to interfit underneath said opposing flanges with the upwardly extending engagement pins interfitting within said holes of said flanges.

3. The apparatus of claim 1 which further comprises a side handle having a pair of horizontally disposed insertion rails, each having an upwardly extending engagement pin, said insertion rails attached to a front rail, and at least one downwardly extending lever handle attached to said front rail, said insertion rails configured for insertion into said transport rack.

4. The apparatus of claim 1 wherein each of said cassettes further comprise a pair of opposing latches for releasably securing said hinged top to said cassette, wherein opposing pressure must be simultaneously applied to each of said opposing latches to release said latches and said top.

5. The apparatus of claim 4 which further comprises a plier rack pivotally mounted within said cassette and configured to lay within said cassette when said hinged top is closed, and to pivot to a generally upright position for holding pliers when said hinged top is open.

6. The apparatus of claim 4 wherein said cassettes are each further configured dimensionally such that either one cassette or a combination of cassettes will completely fill said shelf.

7. The apparatus of claim 4 wherein said plurality of cassettes are of various widths wherein the various widths, from a smallest width to a largest width, are dimensionally configured as whole integer multiples of the smallest width and where the largest width completely fills said shelf.

8. The apparatus of claim 4 wherein said cassettes each further comprise:

a generally rectangular box having opposing side and end walls, a fixed generally flat bottom wall for resting upon a surface, and a hinged top cover, wherein each wall and the top cover are provided with a plurality of holes through which fluid and debris may pass; and wherein said hinge is a double hinge configured to permit said top cover to lay flat upon the same surface which the bottom wall rests upon.

9. The apparatus of claim 8 wherein said double hinge further comprises:
   a first horizontally oriented hinge dividing one of said end walls or one of said side walls into upper and lower halves; and
   a second hinge connecting the upper half of said wall to the top cover.

10. The apparatus of claim 8 wherein said double hinge further comprises:
   a first horizontally oriented hinge interconnected to one of said end walls or one of said side walls and said top cover; and
   a second hinge oriented in juxtaposed relationship to said first hinge dividing said top cover into two interconnected pieces wherein the piece of the top cover attached to said end wall or side wall is of the same general dimensional size as the end wall or side wall to which it is attached to by means of said first hinge.

11. The apparatus of claim 1 wherein said cassettes each further include means for supporting dental or orthodontic tools.

12. The apparatus of claim 1 wherein said cassettes each further include indicia for identifying which dental or orthodontic tools may be contained within said cassettes.

13. The apparatus of claim 12 wherein said indicia further comprises means for color coding said cassettes.

14. The apparatus of claim 1 which further comprises an orthodontic band or dental tray for holding segregated a plurality of variously sized orthodontic bands or dental temporary crowns, said orthodontic band or dental tray comprising bottom plate, a pair of opposing side walls, a front wall, a back wall, and a plurality of interior divider walls, all made of a heat resistant, sterilizable material, and all attached to each other in a configuration to form a tray, open at the top and having a plurality of compartments for holding segregated said plurality of various sizes of orthodontic bands or dental temporary crowns, said bottom plate having a plurality of holes therein configured to drain each of said compartments of fluids, said orthodontic band tray configured dimensionally for insertion onto said shelf in said transport rack.

* * * * *